United States Patent [19]

Sreepada et al.

[11] Patent Number: 5,110,208
[45] Date of Patent: May 5, 1992

[54] MEASUREMENT OF AVERAGE DENSITY AND RELATIVE VOLUMES IN A DISPERSED TWO-PHASE FLUID

[75] Inventors: Sastry R. Sreepada, Clifton Park; Robert R. Rippel, late of Scotia, both of N.Y., by Linda S. Rippel, executrix

[73] Assignee: The United States of America as represented by the United States Department of Energy, Washington, D.C.

[21] Appl. No.: 629,961

[22] Filed: Dec. 19, 1990

Related U.S. Application Data

[63] Continuation-in-part of Ser. No. 285,689, Dec. 16, 1988, abandoned.

[51] Int. Cl.$^5$ .............................................. G01N 21/45
[52] U.S. Cl. ..................... 356/128; 356/134; 356/361
[58] Field of Search ............... 356/128, 130, 134, 135, 356/361

[56] References Cited

U.S. PATENT DOCUMENTS

| | | |
|---|---|---|
| 2,316,239 | 4/1943 | Hare . |
| 2,649,012 | 8/1953 | Schnelle ............... 356/134 |
| 2,703,033 | 3/1955 | Svensson . |
| 2,925,007 | 2/1960 | Silver . |
| 3,071,038 | 1/1963 | Vollmer . |
| 3,368,389 | 2/1968 | Barnett . |
| 3,545,867 | 12/1970 | Rostas . |
| 3,667,846 | 6/1972 | Nater et al. ............... 356/372 |
| 4,381,895 | 5/1983 | Hughes et al. ............... 356/134 |
| 4,659,218 | 4/1987 | de Lasa et al. ............... 356/133 |

FOREIGN PATENT DOCUMENTS 201236 10/1985 Japan ............................ 356/128

OTHER PUBLICATIONS

"Fundamentals of Optics", F. Jenkins and H. White, McGraw Hill, 1957, p. 258, (no month).
IBM Technical Disclosure Bulletin, 13 (1), 258, A. B. Nafarrate, Jun. 1970.

Primary Examiner—Richard A. Rosenberger
Attorney, Agent, or Firm—Judy K. Kosovich; William R. Moser; Richard E. Constant

[57] ABSTRACT

An apparatus and a method are disclosed for measuring the average density and relative volumes in an essentially transparent, dispersed two-phase fluid. A laser beam with a diameter no greater than 1% of the diameter of the bubbles, droplets, or particles of the dispersed phase is directed onto a diffraction grating. A single-order component of the diffracted beam is directed through the two-phase fluid and its refraction is measured. Preferably, the refracted beam exiting the fluid is incident upon a optical filter with linearly varing optical density and the intensity of the filtered beam is measured. The invention can be combined with other laser-based measurement systems, e.g., laser doppler anemometry.

9 Claims, 2 Drawing Sheets

MEASUREMENT OF AVERAGE DENSITY AND RELATIVE VOLUMES IN A DISPERSED TWO-PHASE FLUID

This is a continuation-in-part of application Ser. No. 285,689 filed on Dec. 16, 1988, now abandoned.

FIELD OF THE INVENTION

The present invention relates generally to measuring the average density and relative volumes in a dispersed two-phase fluid, and more particularly, to the use of the refraction of the first order diffraction beam of a finely focused laser beam to measure the average density and relative volumes of a transparent, dispered two-phase fluid.

BACKGROUND OF THE INVENTION

There are many instances in which it is necessary to monitor average density, relative volumes, or properties related to them in a dispersed two-phase system. Processes for which the relative volumes or average density can be used for monitoring or control are especially of interest. Examples of applications include determining relative volumes in distillation in chemical processing, turbidity in environmental monitoring or chemical processing, or the presence or absence of two phases during heat transfer.

Visible light, gamma-rays, X-rays, and neutrons have been used to monitor density in flowing, two-phase fluids. The fact that two-phase fluids scatter light has been taken advantage of, and scattering or attenuation of the beam has been used to monitor the dispersed phase. For most applications, the accuracy obtained with these techniques has been sufficient. A major drawback has been that gamma-rays, X-rays, and neutrons create safety hazards. Though systems based on attenuation are cumbersome and complex, they have been available for many years and are still in use.

Because attenuation produces a logarithmic response, the range of operating conditions that can be monitored is great. However, accuracy and sensitivity are adversely affected by the relative amount of dispersed phase and by the size distribution of the bubbles, droplets, or particles. Measurement errors of 100% frequently occur for relative volumes of gaseous phase as low as 20%. Such large errors are sometimes unacceptable, for example, in nuclear reactor applications.

A method and apparatus for determining the density of fluids is disclosed in U.S. Pat. No. 2,316,239 (Hare). Density is measured by directing a beam of radiation into the fluid. Attenuation or scattering of the radiation, or both, are used to determine its density. A method for determining the percent solids in a saturated solution by measuring the absorption of radiant energy is also disclosed in U.S. Pat. No. 3,368,389 (Barnet).

Laser beams have successfully been used in single-phase and two-phase fluids for the measurement of velocity. These velocity measurements are based on scattering of light by a dispered phase that is either present in the fluid or added to it. The frequency of bursts of scattered light indicates the velocity of the particles as they pass through alternating dark and light bands. *Principles and Practice of Laser-Doppler Anemometry*, F. Durst, A. Melling, J. H. Whitelaw, Academic Press, 1976.

Lasers and collimated light have also been used to measure density in single-phase systems using refraction, diffraction, or a combination of refraction and diffraction.

U.S. Pat. No. 4,381,895 (Hughes et al.) discloses a method and apparatus for determining the concentration of dissolved solids in a flowing solution. A collimated monochromatic light beam is passed through the sample to a light sensor to measure refraction in a single phase. The method described by Hughes could not be used to accurately or sensitively measure average density or relative proportions in a dispersed two-phase system because it does not include a means for causing the entire cross-section of the beam to be refracted by the dispersed phase. If a dispersed phase were present, a portion of the beam would be scattered or attenuated, and the refractivity that would be measured would be that of the continuous phase.

Japan Patent No. 201,236 (Yoshino) discloses the use of refraction of a laser beam in a liquid to monitor refractivity. The output is an electric signal that can be used in a on-line system. The method described by Yoshino could not be used to accurately or sensitively measure average density or relative proportions in a dispersed two-phase system because it does not include a means for making the beam fine enough to be refracted rather than scattered by the dispersed phase.

Using interference patterns greatly increases sensitivity of the measurement of refraction. In Rayleigh's refractometer, a monochromatic light beam is split and passed through different solutions in matched cells. A lens is used to bring the split beams together, and the amount of compensation needed to bring them into phase, as indicated by interference, is used to measure slight differences in refractive index. (Jenkins et al., *Fundamentals of Optics*, pp. 258-259, third edition, McGraw-Hill, New York, 1957. The method described by Jenkins could not be used to accurately or sensitively measure average density or relative proportions in a dispersed two-phase system because it does not include a means for making the beam fine enough to be refracted rather than scattered by the dispersed phase.

Diffraction was used in combination with refraction by A. B. Nafarrate, "Diffraction Refractometer," *IBM Technical Disclosure Bulletin*, 13 (1), 258 (1980). A transmission diffraction grating was placed in a wall of a cell containing a medium. The diffraction pattern for a vacuum or for air was used as a reference. Measurements were made of the distance between the zero order beam and the first order beam. The amount this distance changed allowed the refractive index of the test substance to be determined. Changes in interference patterns is a more sensitive method than simply measuring refraction of a beam. The method described by Naffarate could not be used to accurately or sensitively measure average density or relative proportions in a dispersed two-phase system because it does not include a means for making the beam fine enough to be refracted rather than scattered by the dispersed phase.

The prior art lacks a method for easily, safely, and sensitively monitoring the relative volumes or average density of a transparent, dispersed two-phase fluid.

SUMMARY OF THE INVENTION

In accordance with the present invention, an apparatus for measuring the average density of an essentially transparent, dispersed two-phase fluid having the dispersed phase made up of essentially transparent bubbles, droplets, or particles that have smooth, rounded surfaces which comprises: a source which produces a collimated beam that has a diameter no larger than 1% of the diameter of the bubbles, droplets, or particles of the dispersed phase; a diffraction grating, to which the collimated beam is directed; means for isolating a single-order component of the diffracted beam and directing it through the dispersed two-phase fluid; a means for containing the dispersed two-phase fluid that allows the single-order component of the diffracted beam to pass through, and means for measuring the refraction of the beam by the dispersed two-phase fluid.

The means for measuring refraction of the beam includes an intensity measuring means and a linear density optical filter upon which the refracted beam is incident such that the intensity of a beam that has passed through said filter is dependent on the amount of refraction of the beam.

The means for producing a collimated beam of appropriate diameter can be a double convex lens with a focal length of the lens sufficiently long that the accuracy of the measuring means is preserved or a double convex lens and a collimating lens placed approximately at the focal point of the double convex lens.

Another embodiment of the invention is an apparatus having a single laser with a plurality of colors which are split into their component colors so that average density and relative volumes are measured using one color and other properties are measured using other colors.

The invention is also method for measuring the density of an essentially transparent, dispersed two-phase fluid, wherein the dispersed phase is made up of essentially transparent bubbles, droplets or particles that have smooth, rounded surfaces, comprising the steps of: generating a collimated beam having a diameter no larger than 1% of the diameter of the bubbles, droplets, or particles in the dispersed phase; directing the collimated beam onto a diffraction grating so that a diffracted beam is produced; isolating and directing a single-order component of the diffracted beam through the dispersed two-phase fluid; measuring the deflection of the single-order beam after it has passed through the dispersed two-phase fluid; and determining the average density of the fluid and relative volumes of the two phases from the measured deflection.

DETAILED DESCRIPTION OF THE PREFERRED EMBODIMENT

Figure 1:
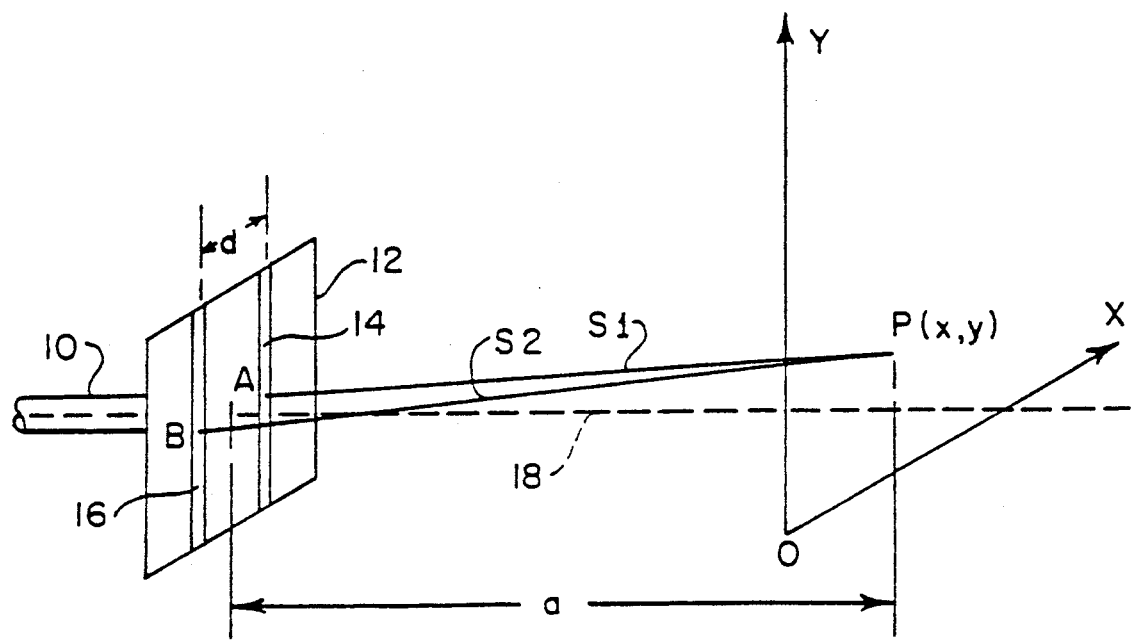
FIG. 1 is a schematic illustration of the operating principle of the present invention.

Before describing the present invention in detail, it is helpful to understand the underlying principle of the present invention as depicted in FIG. 1. Initially, a collimated light beam 10 is incident on a diffraction grating 12, which in this case is transmissive. Considering two adjacent transparent regions 14 and 16, the light distribution of laser beam 10 over the XY plane normal to an incident optic axis 18 and at a Point (x, y) is shown. The difference in optical path lengths for light arriving at P from two points A and B in respective regions 14 and 16 is determined as follows:

$$\Delta L = n(S2 - S1)$$
$$= nxd/a \text{ for } d << a$$

where
 $\Delta L$ = difference in optical path lengths
 n = refractive index along the path
 S1 = distance from A to P
 S2 = distance from B to P
 x = displacement of beam P in the X direction.
 d = separation distance between the two regions 14 and 16
 a = distance between grating 12 and the XY plane
(as described in *Principles of Optics*, Max Born and Emil Wolf, 5th Ed., 1975, Permagon Press, p. 260.)

The first order diffraction maximum occurs when the phase difference $\delta$ is as follows:

$$\delta = (2\pi/\lambda)(nxd/a) = 2\pi$$

where
 $\lambda$ is the wavelength. Then $nx = a\lambda/d$, and
 $x = a\lambda/nd$.

From the above, it is seen that as the refractive index changes, the x coordinate and the position of the first order diffraction maximum changes. Thus, this change of position can be used to measure changes in refractive index, from which can be calculated the relative volumes of dispersed and continuous phases and the average density of a dispersed two-phase fluid.

A diffraction maximum occurs for every x such that $\delta$ is a whole integer multiple of $2\pi$. The whole integer multiple is referred to as the order of the diffraction beam. The first order beam is the most intense of the diffracted beams. Thus, it gives the most intense and finest, and therefore most easily detected signal. The displacement x is greater with higher order beams. Thus, higher orders increase the distance the beam is deflected, providing opportunities for greater sensitivity if used with an appropriate detection system.

Figure 2:
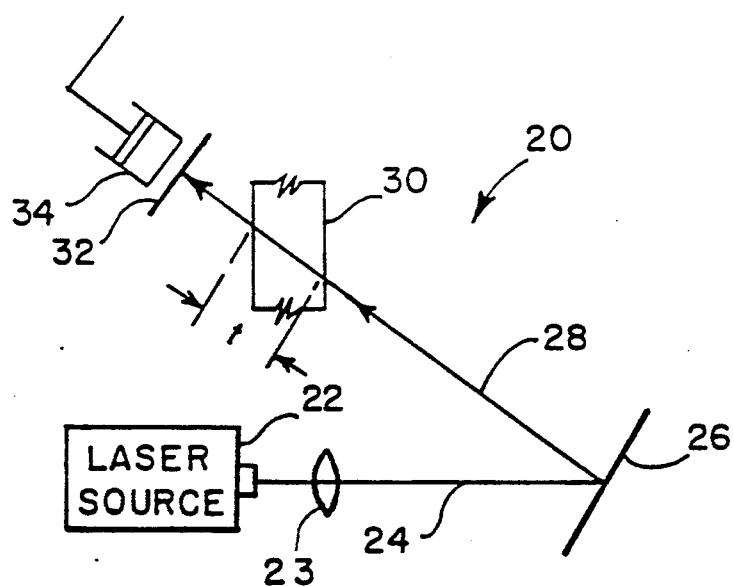
FIG. 2 is a schematic illustration of the apparatus of the present invention.

Depicted in FIG. 2 is a schematic illustration of a density measuring system 20 according to the present invention. Density measuring system 20 includes a source 22 for generating a collimated beam, preferably a laser. The beam diameter is reduced by optics 23 to produce a finer beam 24. The beam is diffracted on diffraction grating 26. Preferably, the optics 23 precedes diffraction grating 26. In this embodiment, diffraction grating 26 is reflective, although it should be appreciated that a transmissive grating is usable with a different configuration. Desirably, the diffraction grating has at least 2,500 lines per millimeter. Through proper orientation of the diffraction grating relative to the sample and the beam, a component 28, preferably the first order component, of the diffracted beam is directed through a suitable transparent portion of a container 30 in which the two-phase fluid to be measured is contained or constrained to flow. As indicated in FIG. 2, diffracted beam 28 has a path length t through the fluid to be measured.

After passing through container 30, diffracted beam 28 is incident on an optical filter 32 which has an optical density that varies linearly and produces a beam with an intensity that varies exponentially. The intensity of light transmitted by optical filter 32 is thus a function of the amount of refraction of diffracted beam 28. This light intensity is then measured by measuring the amplitude of a signal detected by a photomultiplier 34. Such a detection system is desirable because it is readily available and inexpensive.

Of course, when beam position is indicated by beam intensity, attenuation of the beam by the two-phase fluid being measured will introduce errors in the measurement. In most cases, these errors will be negligible. These errors can be further reduced by reducing the beam size, by using a smaller range of optical densities in the optical filter, or by using a measurement system that does not rely on beam intensity to indicate amount of refraction.

Scattering is reduced by making the beam fine. The smaller the beam diameter, the more closely its travel through the dispersed phase approximates travel through a series of flat interfaces. Desirably, the beam diameter is less than 1% of the bubble, droplet, or particle diameter.

The dispersed phase can be solid particles, so long as the particles are transparent and have a shape smooth and round enough that a fine beam would see the solid particles as flat interfaces.

The beam can be made fine in at least two ways. One, it can be passed through a double convex lens. The sample would be at the focal point, which is where the beam diameter is the smallest. Two, the beam can be passed through a combination of lenses, desirably, a double convex lens and a collimating lens, to make the beam parallel as well as fine. The first method approximates the second method if the focal length of the lens is long enough that the beam behaves as if were parallel.

Returning to the calculations, density measuring system 20 is designed to measure the average density of the transparent two-phase fluid in container 30 which fluid consists of a liquid and a gaseous phase. The refractive indices of liquids and gaseous phases are distinctly different. Thus, let n1 and n2 represent the refractive indices of the liquid and gaseous phases, respectively. Where $\alpha$ is the volume fraction of gaseous phase in the measurement fluid, then the refractive index n of the two-phase fluid is given by the following:

$$n = \alpha n2 + (1-\alpha)n1$$

where
n1 = refractive index of the liquid,
n2 = refractive index of the gaseous phase, and
$\alpha$ = volume fraction of gaseous phase in the fluid.

The phase difference for the first order diffraction maximum (as explained above) going from full liquid to full gaseous phase is given by:

$$x1 = (a-t)\lambda/(dn3) + (t\lambda/dn1),$$

and $$x2 = (a-t)\lambda/(dn3) + (t\lambda/dn2)$$

where
n3 = refractive index of air, and
t = travel distance of the beam through the fluid.
Thus, the beam deflection is given by:
$= (t\lambda/d)(1/n1 - 1/n2)$. It should be noted that this is a linear response.

For the transmission of an optical filter 32 with linearly varying density, the signal range is:

$$I2/I1 = 10^{(-t\lambda/d)(1/n1 - 1/n2)D}$$

where
I2 = output with gaseous phase
I1 = output with liquid
D = optical density gradient, such that moving a distance x along the density gradient changes the response by $10^{xD}$.

For any volume fraction, where $I\alpha$ is the output for the two-phase fluid, $$I\alpha/I1 = 10^{(-t\lambda/d)[1/n1 - \{(1-\alpha)/n1 - \alpha/n2\}]D};$$

or $$\log(I\alpha/I1) = -(t\lambda/d)[1/n1 - (1-\alpha)/n1 + \alpha/n2]D = -(\alpha t\lambda/d)[(n1+n2)/n1n2]D$$

or $$(\alpha t\lambda/d)[(n1+n2)/n1n2] = (\log I1 - \log I\alpha)/D$$

$$\alpha = (d/t\lambda)[n1n2/(n1+n2)](\log I1 - \log I\alpha)]D.$$

This same equation would apply if the dispersed phase was the liquid.

In order to obtain the average density from $\alpha$, it is necessary to multiply $\alpha$ by the density of the gaseous phase and add this to $(1-\alpha)$ times the density of the liquid phase. Comparable calculations would be done for other two-phase systems, e.g., liquids in a gaseous phase.

Preferably, the optics, the detecting means, and beam source are mounted in such a way that, as in tomography, the entire cross section of the sample is stationary and is scanned by a moving apparatus. Alternatively, the sample could be moved and the apparatus could remain stationary.

The invention was used to measure density over the entire cross section of three shapes—a glass wedge, a glass rod, and a glass rod with a hole through the center. The system operated as was predicted by the equations.

The system described above would be calibrated and used at a fixed temperature and pressure. The system can also calibrated for a range of temperatures and pressures using the two single-phase points at various temperatures and pressures. If temperature and pressure are determined for two-phase fluids, volume fractions can be calculated from the measurements, the calibrations, and the above equations.

The sensitivity of the system is achieved by focusing the collimated beam so that the beam diameter in the sample is less than one percent of the bubble, droplet, or particle diameter. There are two possible approaches to focusing the beam. The easier is to use a double convex lens with a long focal length, with the sample placed where the beam is most tightly focused. The longer the focal length of the lens, the closer to parallel the beam would be. The more accurate approach is to use a second, collimating lens at the focal point of the first lens to make the beam parallel again.

EXAMPLES

A chlorofluorocarbon, Freon-114, was placed in a flat cell with a 0.1 inch sample thickness. Boiling was induced by heating the sides of the cell using electrical current through a thin film of tin. The film was 85% transparent to the beam. A single 600 mm focal length lens was used to make the beam about 50 microns in diameter in the sample. The bubble diameter was on the order of 0.005 inches. The system was tested from full liquid to full vapor, and behaved as predicted by the equations throughout the range of conditions.

The invention can be combined with other methods. Another application that was reduced to practice was the measurement of the volume fractions and average density of a dispersed, two-phase flowing fluid simultaneously with measurements of horizontal and vertical velocity. The underlying principles of velocity measurements using lasers are described in the Background section, above.

Figure 3:
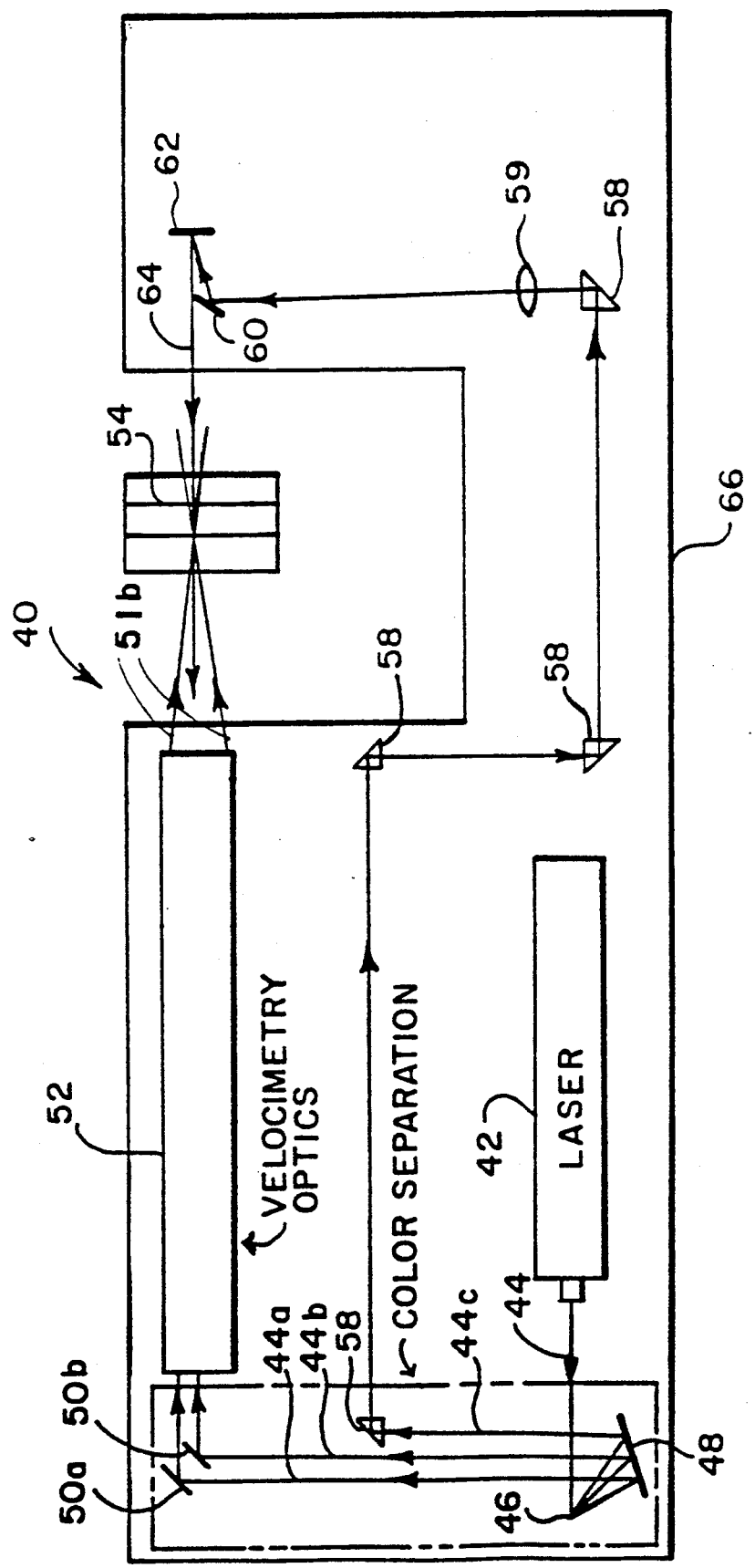
FIG. 3 is a schematic illustration of the simultaneous velocity and density measurement using the present invention.

Commercially available Laser Doppler Velocimetry System (TSI, Inc., St. Paul, Minn.), was used. The configuration used is shown in FIG. 3. A single source 42 generated beam 44. An Argon Ion Laser was used, and the beam 44 was be separated into beams of its three colors using a dispersion prism. Beams 44a, 44b, and 44c correspond to blue, green and near-blue, respectively. These beams were directed by mirrors as shown.

The horizontal and vertical velocities and the average density and relative volumes were measured at the same point in the sample, though other configurations could also be used. Velocimetry optics 52 were used to split each of the two beams so that interference fringes could be formed within cell 54. The beams measuring vertical velocity, the green beams 51 b, are shown converging in the cell. Similar beams were generated (not shown) for the horizontal component, the blue beams. Optical cable or other means can be used to direct the output beams to measuring means.

Laser beam 44c is suitably reflected by right angle prisms 58 to a mirror 60. Mirror 60 is positioned to direct laser beam 44c onto a diffraction grating 62 of the reflective type. Diffraction grating 62 causes the first order component of the diffracted beam to be directed through container 54 for the two-phase fluid. The change of position of the diffracted beam 64 is then measured by the measuring means 56 (the linearly varying optical density filter and photomultiplier, as explained above) in order to determine the density of the two-phase fluid. The refracted beam can be directed to measuring means with mirrors, a fiberoptic cable, or other directing means.

Measuring system 40 was mounted on a laser optics table 66. Table 66 had a means for moving the measuring system while leaving the conduit fixed. This allows the entire cross section of the sample to be scanned or different points along the conduit to be scanned.

Although the present invention has been described with respect to exemplary embodiments thereof, it will be understood by those of ordinary skill in the art that variations and modifications can be effected within the scope and spirit of this invention.

What is claimed is:

1. An apparatus for measuring the average density of an essentially transparent, dispersed two-phase fluid having a dispersed phase made up of essentially transparent bubbles, droplets, or particles that have smooth, rounded surfaces, comprising:
    a source which produces a collimated beam that has a diameter no larger than 1% of the diameter of the bubbles, droplets, or particles of the dispersed phase;
    a diffraction grating, to which the collimated beam is directed;
    means for isolating a single-order component of the diffracted beam and directing it through the dispersed two-phase fluid;
    containing means for the dispersed two-phase fluid that allows the single-order component of the diffracted beam to pass through, and
    measuring means for determining the refraction of the beam by the dispersed two-phase fluid.

2. An apparatus for measuring average density as in claim 1 wherein said means for measuring refraction of the beam includes an intensity measuring means and a linear density optical filter upon which the refracted beam is incident such that the intensity of a beam that has passed through said filter is dependent on the amount of refraction of the beam.

3. An apparatus as in claim 2 wherein the intensity measuring means is a photomultiplier.

4. An apparatus as in claim 1 wherein the source that produces the collimated beam contains a double convex lens for reducing the cross section of a collimated beam, and wherein the focal length of the lens is sufficiently long that the accuracy of the measuring means is preserved.

5. An apparatus as in claim 1 wherein the source that produces the collimated beam contains a double convex lens and a collimating lens placed approximately at the focal point of the double convex lens.

6. An apparatus as in claim 1 wherein the single-order component of the diffracted beam is the first order component and the diffraction grating has at least 2,500 lines per millimeter.

7. An apparatus as in claim 1 wherein a single laser with a plurality of colors is split into its component colors and average density and relative volumes are measured using one color and other properties are measured using other colors.

8. The apparatus of claim 7 wherein there are three colors and the other properties measured are horizontal velocity and vertical velocity.

9. A method for measuring the density of an essentially transparent, dispersed two-phase fluid, wherein the dispersed phase is made up of essentially transparent bubbles, droplets or particles that have smooth, rounded surfaces, comprising the steps of:
    generating a collimated beam having a diameter no larger than 1% of the diameter of the bubbles, droplets, or particles in the dispersed phase;
    directing the collimated beam onto a diffraction grating so that a diffracted beam is produced;
    isolating and directing a single-order component of the diffracted beam through the dispersed two-phase fluid;
    measuring the deflection of the single-order beam after it has passed through the dispersed two-phase fluid; and
    determining the average density of the fluid and relative volumes of the two phases from the measured deflection.

* * * * *